United States Patent
Balistreri et al.

(10) Patent No.: US 7,947,946 B2
(45) Date of Patent: May 24, 2011

(54) OPTICAL SYSTEM FOR MAPPING SIGNAL LIGHT ONTO A DETECTOR

(75) Inventors: Marcello Balistreri, Rosmalen (NL); Derk Jan Wilfred Klunder, Geldrop (NL); Maarten Van Herpen, Heesch (NL)

(73) Assignee: Koninklijke Philps Electronics N.V., Eindhoven (NL)

( * ) Notice: Subject to any disclaimer, the term of this patent is extended or adjusted under 35 U.S.C. 154(b) by 628 days.

(21) Appl. No.: 11/909,638

(22) PCT Filed: Mar. 27, 2006

(86) PCT No.: PCT/IB2006/050917
§ 371 (c)(1), (2), (4) Date: Sep. 25, 2007

(87) PCT Pub. No.: WO2006/103612
PCT Pub. Date: Oct. 5, 2006

(65) Prior Publication Data
US 2010/0140464 A1    Jun. 10, 2010

(30) Foreign Application Priority Data
Mar. 30, 2005 (EP) .................................. 05102521

(51) Int. Cl.
*G01D 5/36* (2006.01)
(52) U.S. Cl. ............. 250/237 G; 250/208.1; 359/558; 359/566; 359/571
(58) Field of Classification Search ............... 250/214.1, 250/214 R, 208.1, 208.2, 216, 226, 201.1, 250/237 G, 221; 359/74, 576, 579, 570, 571, 565, 656, 558, 566
See application file for complete search history.

(56) References Cited

U.S. PATENT DOCUMENTS

| | | | |
|---|---|---|---|
| 3,728,014 A * | 4/1973 | Rosenblum | 353/38 |
| 4,708,436 A | 11/1987 | Kleinknecht | |
| 6,312,961 B1 | 11/2001 | Voirin et al. | |
| 2002/0005938 A1* | 1/2002 | Omura | 355/53 |
| 2002/0054558 A1* | 5/2002 | Freeman | 369/112.07 |
| 2002/0159377 A1 | 10/2002 | Saito et al. | |
| 2004/0130804 A1 | 7/2004 | Mimori | |
| 2006/0056027 A1* | 3/2006 | Feldman | 359/562 |

FOREIGN PATENT DOCUMENTS
EP  1720340 A1  11/2006
WO  02059583 A1  8/2002

* cited by examiner

Primary Examiner — Georgia Y Epps
Assistant Examiner — Francis M Legasse, Jr.

(57) ABSTRACT

The invention relates to an optical system that particularly allows an improved detection of signal light propagating from a light source (1) through a flat glass substrate (11). SC-modes of this signal light that would normally be totally internally reflected at the backside (10) of the substrate (11) are coupled out by a first diffractive optical element DOE (21). To map all signal light leaving the substrate (11) onto a single target location (51), a focusing lens (31) and a second DOE (41) are disposed in the optical path behind the substrate (11). The DOEs (21, 41) may for example be a ID sinusoidal grating or a 2D blaze grating. The optical system may particularly be applied in an investigation apparatus for detecting multiple spots of a fluorescent sample material.

7 Claims, 2 Drawing Sheets

OPTICAL SYSTEM FOR MAPPING SIGNAL LIGHT ONTO A DETECTOR

The invention relates to an optical system and a method for the mapping of signal light from at least one light source onto a target location.

In the WO 02/059583 A1 a detailed analysis is given of the propagation of signal light from a luminescent sample through a glass substrate. The analysis shows that a large part of the intensity is contained in so-called "SC-modes" which by definition comprise signal light that reaches the backside of the glass substrate (i.e. the side opposite to the sample) under angles of total internal reflection. Signal light of the SC-modes is therefore normally lost for detection purposes. In order to prevent this loss, it is proposed in the WO 02/059583 A1 to dispose diffractive optical elements on the backside of the glass substrate which couple light of the SC-modes out of the glass substrate by diffraction. A problem with this approach is however that the signal light leaving the glass substrate is spread over a large range of angles which must be covered by a detector to collect all available signal light. Moreover, the emissions of signal light from different light sources mix and can therefore not be spatially separated by a detector.

Based on this situation it was an object of the present invention to provide means for an improved, particularly a spatially resolved processing of signal light.

This object is achieved by an optical system according to an embodiment and a method according to another embodiment. Preferred embodiments are disclosed in the dependent claims.

According to its first aspect, the invention comprises an optical system with an imaging unit for the mapping of light (called "signal light" in the following for purposes of reference) from at least one light source onto a target location, wherein the target location corresponds to the image of the light source. The light source may for example be a luminescent spot of sample material in a (bio-)chemical investigation or a technical component like an LED. The imaging unit typically focuses signal light onto an image plane according to the principles of geometrical optics. It may particularly comprise one or more lenses, wherein the numerical aperture (NA) of the imaging unit (i.e. the lens facing the light source) is preferably larger than 0.8, most preferably as large as the index of the medium surrounding said lens. The optical system further comprises the following components:
  a) At least one first diffractive optical element (abbreviated DOE in the following) which is located "in front of" the imaging unit with respect to the optical path of the signal light, i.e. signal light will be diffracted by said first DOE before entering the imaging unit.
  b) At least one second DOE that is located "behind" the imaging unit with respect to the optical path of the signal light, i.e. signal light has to leave the imaging unit before it can enter the second DOE. Suitable realizations of the first and second DOE will be described in more detail in the following with respect to preferred embodiments of the invention.

An optical system of the aforementioned kind has the advantage to provide a desired functionality of the first DOE, which may for example be a wavelength filter with a pronounced transmission for a small wavelength regime, while at the same time less desired effects of the first DOE can be compensated by the second DOE.

The first DOE and the second DOE may particularly be arranged and designed such that the effect which the first DOE has on the path of light rays passing through it is reversed by the second DOE. With other words the optical system as a whole images the input spot in a similar way as if there would be no gratings present and the imaging unit (e.g. lens) would image the input spot while still benefiting from the first DOE. Thus desired effects of the first DOE on the signal light (e.g. a wavelength filtering) are preserved while simultaneously an undisturbed optical imaging of this light can be achieved.

The first and the second DOE may in principle have a different design (i.e. form and/or dimension). In a preferred embodiment, the first and the second DOE are however identical in design.

According to another optional embodiment, the first and the second DOE are used in a mirrored arrangement. If the DOEs are identical, too, the second DOE may then reverse the effects that the first DOE had on the optical path of the signal light.

In a preferred realization of the invention, the optical system comprises additionally an at least partially transparent substrate with a (curved or flat) backside, wherein signal light from the light source can be coupled into the substrate and wherein at least a part of this signal light can leave the substrate through the backside. The "backside" is one of the sides of the substrate which is given this name for reference and based on a view from the light source. The location of the light source with respect to the substrate is not restricted in any way; the light source may particularly be remote from, adjacent to, or even embedded in the substrate. In many cases the substrate will be a substantially flat plate made from glass or a transparent polymer. Moreover, the first diffractive optical element DOE is located at the backside of the substrate and adapted to couple signal light of SC-modes out of the substrate. "SC-modes" comprise by definition signal light that would be totally internally reflected at the backside if the first DOE would not be present. A detailed description of the SC-modes and suitable realizations of the first DOE can be found in the WO 02/059583 A1. The optical system (particularly its imaging unit and the second DOE) may particularly be designed such that more than 80%, preferably more than 90%, most preferably all of the signal light of the SC-modes that was coupled out of the substrate will be directed to the target location.

An optical system of the aforementioned kind has the advantage to provide a high yield of signal light due to the first DOE that couples out light which would normally be captured inside the substrate. Furthermore, the spreading of the signal light which is introduced by the first DOE and which corrupts the normal geometrical imaging of the light source is reversed by the second DOE such that finally the signal light of the SC-modes (or at least a large part of it) reaches the target location. A detector for measuring signal light from the light source can therefore be kept smaller than in the case of unhindered light spreading. Moreover, it is possible to image a plurality of different light sources in a spatially resolved way onto distinct target locations without (or with reduced) crosstalk.

The first DOE and/or the second DOE may particularly be one-dimensional gratings which by definition have a (periodic) structure in a first direction and a constant form in a second, perpendicular direction. Alternatively, the first and/or second DOE may be two-dimensional gratings with (periodical) structures in two perpendicular directions.

Every diffractive optical element shows a characteristic intensity pattern of the diffracted light when it is illuminated with a plane wave of light, wherein said pattern is determined by the design parameters of the DOE (for example by the width and distance of the slits in a multi-slit grating). The intensity pattern can be described by the diffractive orders which classify the effects of constructive or destructive interference taking place behind the DOE. In the case of the optical system described here, the first and/or the second DOE are preferably designed such that more than 80%, most preferably more than 95% of the intensity of diffracted light leaving the DOE is contained in one diffractive order. It is therefore possible to concentrate on the signal light in said order, i.e. to design the optical system such that light of this order is directed to the target location while light propagating in other diffractive orders may be neglected.

The optical system may be used for many different tasks. For an important class of applications, the optical system may comprise a sample chamber adjacent to the substrate mentioned above, wherein a luminescent sample material can be provided in said sample chamber. In this case the signal light from the luminescent (e.g. fluorescent) sample material can be collected with a high efficiency and mapped in a spatially resolved way onto the target location.

According to another development of the invention, the optical system comprises an array of detector elements disposed at the target location (i.e. disposed such that the target location lies in the array). The array of detector elements may particularly be the sensitive area of a CCD camera. With an array of detector elements it is possible to distinguish signal light from different light spots because the images of the spots are mapped on different detector elements of the array.

The invention further comprises a method for mapping signal light from at least one light source onto a target location corresponding to the image of the light source, comprising the following steps:
   a) Diffracting signal light a first time, for example with a first DOE.
   b) Imaging said diffracted signal light to a target location according to the principles of geometrical optics.
   c) Diffracting said focused signal light for a second time (e.g. with a second DOE) such that (all or a part of) it interferes constructively at the target location, which results in a spot at said location (i.e. an image of the light source).

The method may optionally comprise the following further steps:
   Coupling signal light from the light source into a substrate, said substrate having a backside through which the signal light may at least partially leave it.
   Coupling so-called SC-modes of the signal light out of the substrate by the first diffraction process, wherein the "SC-modes" by definition comprise light that would be totally internally reflected at the backside of the substrate if no diffraction would take place.

The method comprises in general form the steps that can be executed with an optical system of the kind described above. Therefore, reference is made to the preceding description for more information on the details, advantages and improvements of that method.

These and other aspects of the invention will be apparent from and elucidated with reference to the embodiment(s) described hereinafter.

In the following the invention is described by way of example with the help of the accompanying drawings in which.

Figure 1:
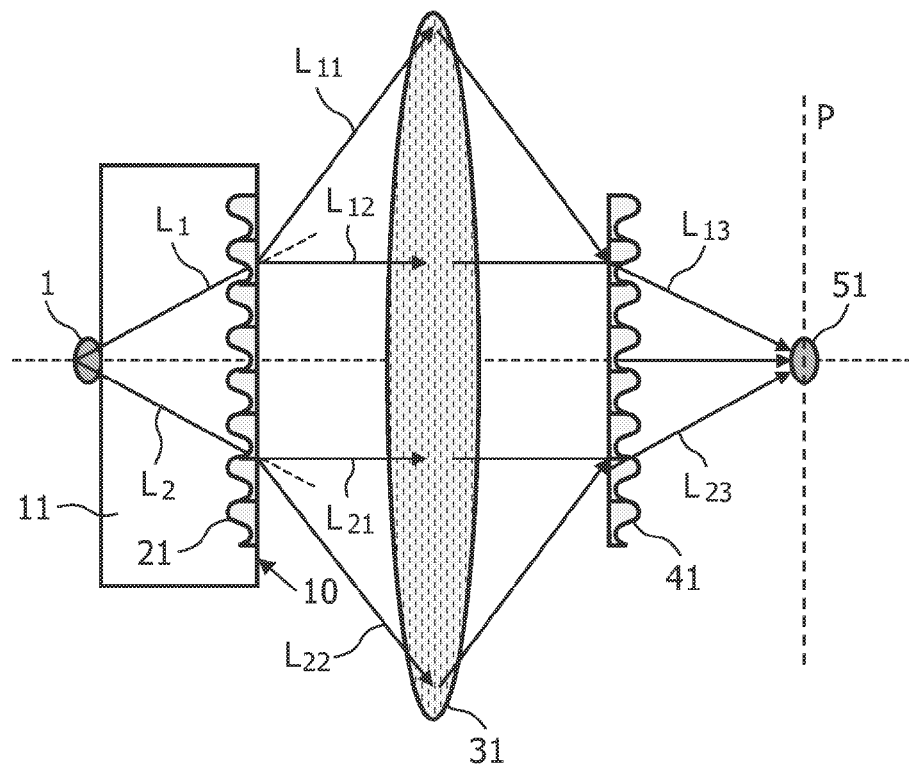
FIG. 1 shows an optical system according to the present invention with sinusoidal gratings.

FIG. 1 shows schematically the setup of an optical system according to a preferred embodiment of the present invention. A light source 1 is disposed adjacent to a transparent substrate 11, which may for instance be a flat glass plate. The light source 1 may be a spot of sample material to be investigated that emits signal light (e.g. fluorescence). It should be noted, however, that such an investigation system is only one example for the application of the present invention.

A detailed analysis of the propagation of signal light emitted by luminescent particles 1 through a glass substrate 11 can be found in the WO 02/059583 A1 which is incorporated into the present application by reference. According to this analysis a considerable part of the signal light emitted by the light source 1 is contained in the SC-modes, which are indicated by the representative rays $L_1$, $L_2$ and which comprise the signal light that reaches the backside 10 of the glass substrate 11 under angles of total internal reflection (provided that the medium contacting the backside 10 has a lower index than the glass substrate, for example if it is air). Thus the light of the SC-modes is normally captured inside the glass substrate 11 (leaving it perhaps in sideward direction) and lost for detection purposes.

To make the light of the SC-modes usable, a first diffractive optical element 21 is disposed at the backside 10 of the glass substrate 11 that couples out the light $L_1$, $L_2$ contained in the SC-modes. In the embodiment of FIG. 1, said diffractive optical element is realized by a (one-dimensional) sinusoidal grating 21 which may for example be etched into the glass surface.

Figures 2, 3:
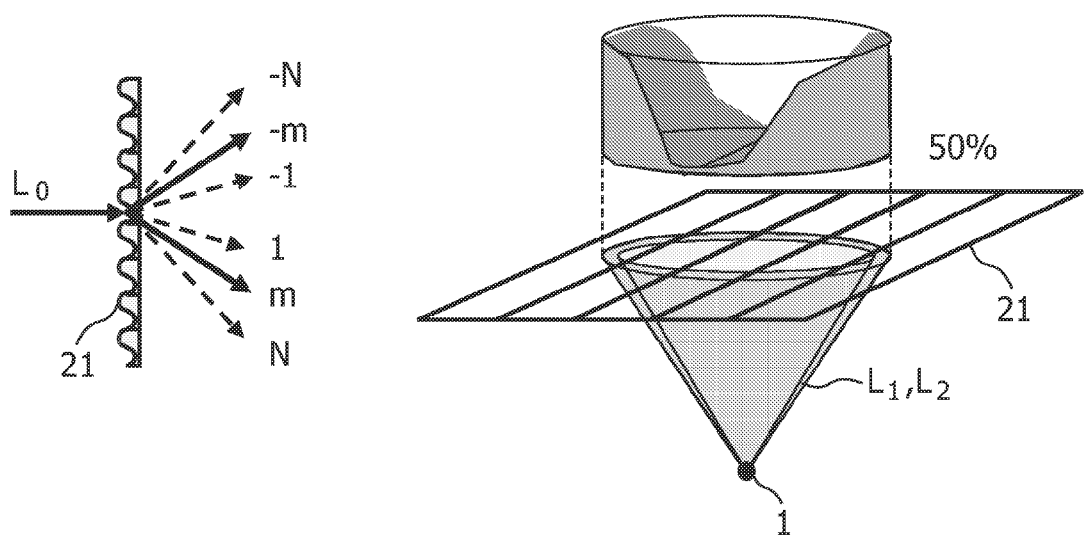
FIG. 2 shows the principle of diffraction at a sinusoidal grating for the transmitted diffraction orders.
FIG. 3 illustrates in a perspective view the intensity distribution of light in the SC-modes diffracted by a one-dimensional sinusoidal grating.

The working principle of a sinusoidal grating 21 is schematically shown in FIG. 2. When irradiated with a planar light wave $L_0$, said light is diffracted by the grating 21 and propagates behind the grating 21 with a certain intensity pattern in all directions. Different directions of this pattern are characterized by the order $-N, \ldots -m, \ldots -1, +1, \ldots +m, \ldots +N$ of interference and carry different light intensities. For the purpose of the present invention, the grating 21 (or any other grating used instead of it) is designed such that substantially all of the light will be contained in one dominating diffractive order, for example the m=2nd order (indicated by fat arrows in FIG. 2). Moreover, the reflection of the gratings will preferably be made as small as possible.

In the optical system shown in FIG. 1, a sinusoidal grating 21 of the kind shown in FIG. 2 is irradiated by the SC-modes $L_1$, $L_2$ under the angle of the dominating order of this grating. In this case the light of the SC-mode $L_1$ is coupled out of the glass substrate 11 and propagates behind the substrate mainly in a ray bundle $L_{11}$ (corresponding to order $-m$ in FIG. 2) and a ray bundle $L_{12}$ (corresponding to the incident light $L_0$ in FIG. 2). In a similar way the second light beam $L_2$ propagates in ray bundles $L_{21}$, $L_{22}$ behind the glass substrate 11.

In the arrangement shown in FIG. 1, all of the signal light emitted by the light source 1 and coupled out of the glass substrate 11 is captured by a focusing lens 31 and converges behind said lens towards an image plane P (without the presence of grating 41 on a substrate identical to substrate 11, the image plane can be at a different position). Without the sinusoidal grating 41 and lens 31, the diffracted orders $L_{11}$, $L_{12}$, $L_{21}$, $L_{22}$ would not be diffracted into the orders $L_{13}$ and $L_{23}$ (which are the reverse of rays $L_1$ and $L_2$ with the proper phase such that light source 1 is imaged as spot 51). This would result in ghost spots spread across the image plane P and lead to undesirable crosstalk if a plurality of light sources were present.

In order to prevent the aforementioned crosstalk, the optical system of FIG. 1 comprises a second diffractive optical element DOE in the form of a sinusoidal grating 41 that is disposed in a mirrored arrangement with respect to the lens 31 and the first grating 21. Moreover, the second sinusoidal grating 41 is preferably of the same type and dimensionality as the first grating 21. The second grating 41 inverts effects of the first grating 21 on the optical path of signal light from the light source 1 (i.e. on the virtually prolonged path of ray bundles $L_1$, $L_2$), so that there are two light bundles $L_{13}$, $L_{23}$ behind the second grating 41 which converge to the target location 51. Thus all signal light emitted by the light source 1 is concentrated at one image spot, and a plurality of light sources can be mapped spatially resolved onto the image plane P.

The function of an arrangement according to FIG. 1 relies on the fulfillment of the reciprocity principle and on the fact that all of the diffracted light $L_{11}$, $L_{12}$, $L_{21}$, $L_{22}$ is captured by the lens 31, i.e. that this lens has a sufficiently large NA. Due to the reciprocity principle (or principle of reversibility, cf. E. Hecht, "Optics," 2nd edition, Addison-Wesley, Reading, Mass., chapter 4, 1987), for a given configuration with a number of input rays (plane waves) and output (e.g. scattered, reflected, transmitted) rays, reversing the direction of all the output rays results in the input rays now traveling in the reverse direction.

FIG. 3 shows in a perspective sketch the cone of light $L_1$, $L_2$ in the SC-modes emitted by the light source 1 and diffracted by a one-dimensional sinusoidal grating 21. As is illustrated by the intensity distribution above the grating 21, an amount of about 50% of the light intensity in the SC-modes is coupled out by the grating 21. With a two-dimensional sinusoidal grating, a larger angle range can be obtained to couple the light out, compared to a 1D grating. This would however lead to the generation of five spots, four of which would be ghost spots.

Figure 4:
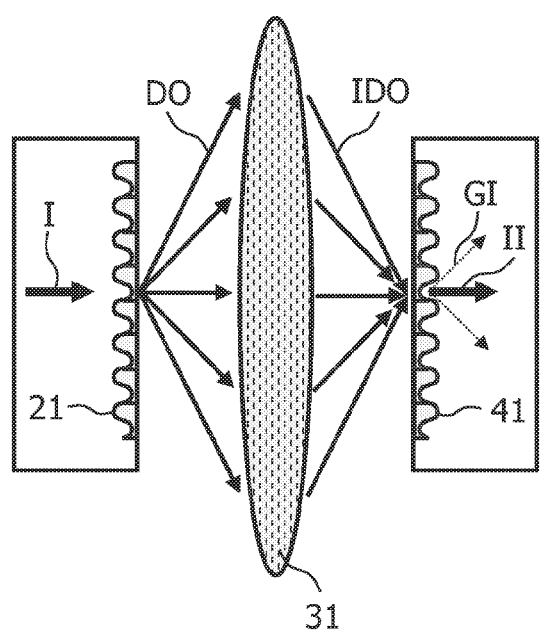
FIG. 4 illustrates a setup used to calculate the intensity distribution of the optical system.

FIG. 4 shows the principal setup of an optical system according to the present invention which allows to use the functionality of a first grating 21 without compromising for imaging quality, because the second grating 41 folds back the orders to the original image without generating ghost spots. The first grating 21 can e.g. be a grating outcoupler that frustrates total internal reflection, or it can be a wavelength filter with pronounced transmission for a small wavelength regime.

For a more detailed numerical analysis, the model system of FIG. 4 is assumed to consist of two identical gratings 21, 41 with a sinusoidal groove in glass that are separated by the lens 31. The diffraction pattern of grating 21 is imaged 1-1 on grating 41. The arrows indicate rays of input light I, diffracted orders DO, diffracted orders imaged by lens IDA, imaged input II, and ghost image GI. Moreover, the following parameters were assumed:

Refractive indexes: Glass, n=1.5; Air, n=1;
Grating: Period of 10 microns and grating depth of 250 nm.
Wavelength: 1 micron.
Polarization: TE
Input: Plane wave at normal incidence.

The diffraction efficiencies of the gratings were calculated using a rigorous grating solver. As an approximation only the first 5 diffraction orders (orders −2, −1, 0, 1, 2) of grating 21 were included. From the following Table 1, it follows that this is a reasonable approximation.

TABLE 1

| Order | Diffraction Efficiency of first grating |
|---|---|
| 4 | 1E−08 |
| 3 | 1.22E−06 |
| 2 | 0.000328 |
| 1 | 0.035778 |
| 0 | 0.887649 |
| −1 | 0.035787 |
| −2 | 0.000331 |
| −3 | 1.25E−06 |
| −4 | 1E−08 |

The total transmission of the first grating 21 is 96%. Thus 4% of the power is in the reflected orders being in good agreement with the Fresnel reflection on a glass/air interface for normal incident light (4%).

Using the 5 orders as input for the second grating 41, the optical power in the orders in the glass layer of grating 41 were calculated, wherein the order having the same angle as the input is denoted by "II" and the other orders are considered as ghost spots (GI). For a good image, the amount of power in II should be large compared to the power of GI.

Lens with NA=1:

Table 2 shows the fraction of input in orders behind grating 41 classified into ghost images (GI) and image (II):

| Class | Order | Fraction of input |
|---|---|---|
| GI | −2 | 0.00% |
| GI | −1 | 0.00% |
| II | 0 | 92.09% |
| GI | 1 | 0.00% |
| GI | 2 | 0.00% |

From Table 2 it can be concluded that using a lens with NA=1 results in a virtually perfect image of the input beam, with no ghost images. The total amount of the input power in the central spot (II) is slightly smaller than the power resulting after two Fresnel reflections at a glass-air interface for normal incident light: 92.16%. This small difference can probably be attributed to the fact that not all diffraction orders generated by grating 21 were included.

Lens with NA<1 that is Capable of Imaging First Three Orders: −1, 0, 1:

Table 2 shows the fraction of input in orders behind grating 41 classified into ghost images (GI) and image (II):

| Class | Order | Fraction of input |
|---|---|---|
| GI | −2 | 0.03% |
| GI | −1 | 0.00% |
| II | 0 | 91.94% |
| GI | 1 | 0.00% |
| GI | 2 | 0.03% |

The fraction in first order ghost spots is still virtually zero; this indicates that power in first order ghost spot is determined by interference between
i) contribution that experienced first order diffraction by grating 21 and fundamental order diffraction by grating 41, and ii) contribution that experienced fundamental order diffraction by grating 21 and first order diffraction by grating 21.

Lens with NA<1 that is Incapable of Imaging Orders≠0:

Table 4 shows the fraction of input in orders behind grating 41 classified into ghost images (GI) and image (II):

| Class | Order | Fraction of input |
|-------|-------|-------------------|
| GI | -2 | 0.03% |
| GI | -1 | 3.18% |
| II | 0 | 78.79% |
| GI | 1 | 3.18% |
| GI | 2 | 0.03% |

Further reducing the NA of the lens to the point that it can only image the fundamental order results in an image similar to the image of a single spot.

The simulations show that using two identical gratings where the diffraction pattern of the first grating is imaged on the second grating, it is possible to image the input of the first grating behind the second grating without the presence of ghost spots provided that the NA of the imaging lens is sufficiently high in order to allow adjacent diffraction orders to interfere. Based on this fact, one can for example use the first diffraction grating as an outcoupling grating that frustrates total internal reflection, and by using the second grating collect each angle of the radiation into a single diffraction order one achieves a virtually perfect image of fluorescent beads. Because the image behind the 2nd grating is essentially perfect, one can image/spatially resolve multiple beads using this method.

Because the principles described above work for a sinusoidal grating irrespective of the grating period and because any grating shape can be expressed as a sum of sinusoidal gratings, the described principles also work for any other grating shape. Thus blazed gratings could for instance be used instead of the sinusoidal gratings 21, 41 in FIG. 1.

Figure 5:
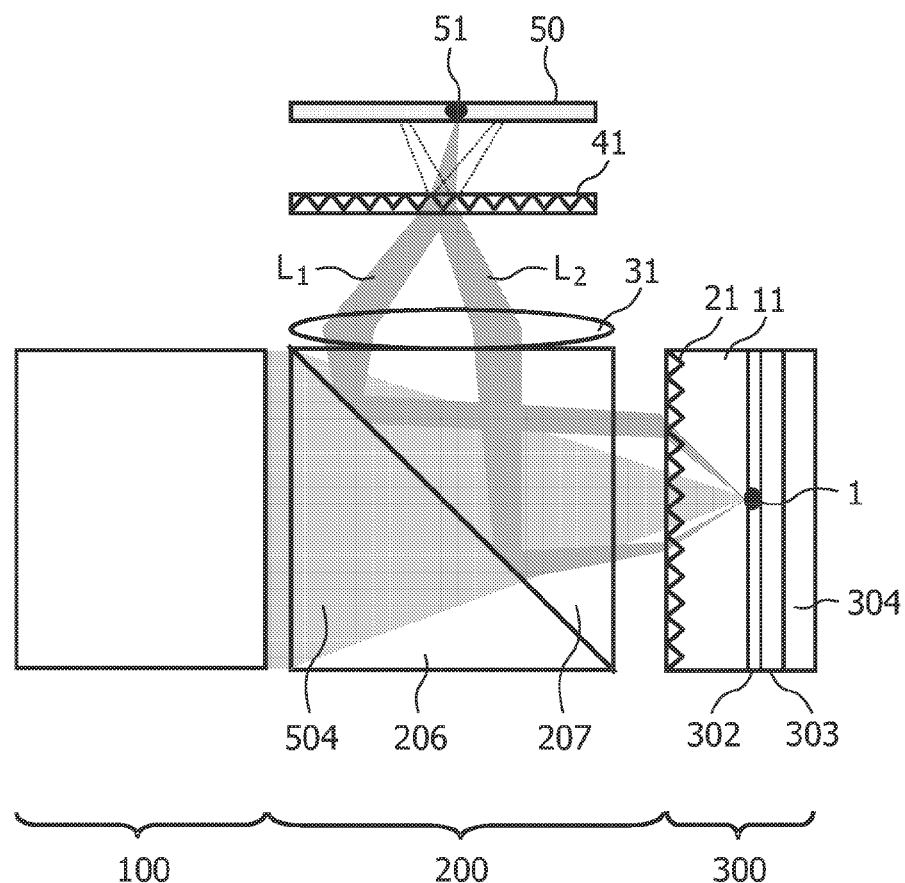
FIG. 5 shows an investigation apparatus for the investigation of luminescent material with an optical system according to the present invention.

FIG. 5 shows the application of the optical system described above in an investigation apparatus. Said apparatus principally comprises a multiple-spot generator MSG 100 for the generation of an array of sample light spots within the sample layer 302 of a biosensing unit 300 (wherein only one representative sample light spot 1 of the array is shown in FIG. 5). The MSG 100 may for example be realized by a light source irradiating an array of apertures, thus producing an array of source light spots at the output of the MSG. Excitation light 504 from one source light spot of the MSG 100 is focused (with optics not shown in FIG. 5) onto a sample light spot 1 in the sample layer 302 of a sample chamber 303, wherein said sample chamber 303 is formed between a glass substrate 11 and a cover plate 304. The sample chamber 303 contains a fluid with a fluorescent sample material, the fluorescence of which is excited in the sample light spot 1 by the excitation light 504. A part of the stimulated fluorescence light then propagates into the glass substrate 11 as was discussed above for a general arrangement of this kind. According to the principles described above, fluorescent signal light that propagates in the SC-modes is coupled out of the substrate 11 by a first diffractive optical element 21, for example a sinusoidal grating. In FIG. 5, only the ray bundles $L_1$, $L_2$ of the fluorescence in the SC-modes are shown. The light of these bundles is reflected at the backside of a prism 207 of a dichroic beam splitter 206, 207 which is designed such that the excitation light 504 may pass unaffected while the fluorescence light is reflected. As was described above, a focusing lens 31 together with a second diffractive optical element 41 focus all the signal light emitted by a sample light spot 1 onto a single image spot 51 in an array 50 of detector units (e.g. a CCD array). Thus each of a plurality of sample light spots in the sample layer 302 will be mapped to a different location (pixel) on the array 50 allowing to measure them separately and with a high yield.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An optical system with an imaging unit for mapping signal light from at least one light source on a target location, comprising:
    at least one first sinusoidal diffractive optical element (DOE) located in front of the imaging unit with respect to the optical path of the signal light;
    at least one second sinusoidal diffractive optical element (DOE) located behind the imaging unit with respect to the optical path of the signal light, wherein the at least one second sinusoidal DOE is configured so that the effect the first sinusoidal DOE has on the path of light rays passing therethrough is reversed by the second sinusoidal DOE;
    a substrate comprising a backside, wherein the first sinusoidal diffractive optical element DOE is located at the backside of the substrate and is adapted to couple out signal light of SC-modes, which comprise signal light that would otherwise be totally internally reflected at the backside; and
    a dichroic beam splitter disposed between the first sinusoidal diffractive optical element and the second sinusoidal optical element, and configured to reflect the SC-modes.

2. The optical system of claim 1, wherein the first sinusoidal DOE and the second sinusoidal DOE are of identical design and/or that they are disposed in a mirrored arrangement with respect to the imaging unit.

3. The optical system of claim 1, wherein the first DOE and/or the second DOE is a one-dimensional or a two-dimensional grating.

4. The optical system of claim 1, wherein the first DOE and/or the second DOE are designed such that more than 80%, preferably more than 95% of the output intensity is contained in one diffractive order.

5. The optical system according to claim 1, wherein the imaging unit comprises a lens, preferably a lens with a numerical aperture NA of more than 0.8, most preferably as large as the index of the medium surrounding the lens.

6. The optical system according to claim 1, wherein an array of detector elements is disposed at the target location.

7. The optical system according to claim 2, wherein it comprises a sample chamber adjacent to a substrate in which a luminescent sample material can be provided.

* * * * *